United States Patent [19]

Gardocki

[11] 4,207,340

[45] Jun. 10, 1980

[54] ANALGESIC POTENTIATION

[75] Inventor: Joseph F. Gardocki, Doylestown, Pa.

[73] Assignee: McNeilab, Inc., Fort Washington, Pa.

[21] Appl. No.: 970,685

[22] Filed: Dec. 18, 1978

[51] Int. Cl.$^2$ .................. A61K 31/19; A61K 31/165
[52] U.S. Cl. ..................................... 424/317; 424/324
[58] Field of Search ................................. 424/317, 324

[56] References Cited

PUBLICATIONS

Merck Index, 7th Ed. (1960), pp. 537–538.
Merck Index, 9th Ed. (1976) p. 1164.
Merck Index, (1976), pp. 6 and 1164.
USAN and the USP Dictionary of Drug Names, 1978, p. 12.
Physician's Desk Reference, 1978, p. 1079.

*Primary Examiner*—Stanley J. Friedman

[57] ABSTRACT

A method of producing analgesia by administering (Z)-5-fluoro-2-methyl-1-{[4-methylsulfinyl)-phenyl]methylene}-1H-indene-3-acetic acid or a salt thereof together with acetaminophen and compositions therefor.

8 Claims, No Drawings

ANALGESIC POTENTIATION

This invention is directed to improved methods and compositions for producing analgesia.

BACKGROUND OF THE INVENTION

One of the long existing primary goals of medicine is the relief of pain. Relief is sought most generally by the administration of analgesic drugs which produce a state of decreased awareness of the sensation and increase of the pain threshold.

Almost all potent analgesics evoke reactions other than the relief of pain. Some of the reactions are gastrointestinal disturbances, nausea, constipation and vomiting. Among the more serious of the side reactions and one frequently found in analgesic drugs is respiratory depression. Thus, in the use of analgesics in man, considerations other than the primary effect (analgesia), must be made and drugs for pain relief are sought which have maximum analgesic effect accompanied by minimum side reactions. It is difficult to satisfy these requirements with a single chemical entity since generally a potent analgesic has accompanying serious side reactions while a drug with little or no side effects are generally less effective as an analgesic.

Thus, there is a continuing search for a combination of two or more drugs whereby the total quantity of drug can be reduced and which can be employed in such proportions as to produce maximum analgesic effect with little or no side effects. When one or both of the components of a combination is known to possess pain relieving properties but these properties are increased many fold, the net effect of the combination is commonly referred to as "potentiation."

Acetaminophen (p-acetaminophenol) is recognized as an analgesic agent with useful and safe antinociceptive properties. However, in certain instances, high doses must be employed to effectively reduce pain. (Z)-5-Fluoro-2-methyl-1-{[4-methylsulfinyl)phenyl]methylene}-1H-indene-3-acetic acid is known by the generic name of "sulindac" for use as an anti-inflammatory agent; it also has analgesic properties. However, the effect of the combination of these two drugs on the analgesic properties was not known prior to our work.

STATEMENT OF THE INVENTION

The present invention concerns an improved method of producing analgesia made possible by the discovery that a potentiation of analgesic or antinociceptive properties of (Z)-5-fluoro-2-methyl-1-{[4-(methylsulfinyl)-phenyl]methylene}-1H-indene-3-acetic acid or its salt is produced by administration with acetaminophen in specific proportions. The use of the combination in the suppression of pain is unexpectedly much greater than that which would result from simply the additive effect of the components.

DESCRIPTION OF THE INVENTION

The novel and unexpected superior analgesic properties may be achieved by the simultaneous or sequential oral administration of (1) acetaminophen and (2) a 1H-indene-3-acetic acid compound, said compound being (Z)-5-fluoro-2-methyl-1-{[4-(methylsulfinyl)phenyl]methylene}-1H-indene-3-acetic acid represented by the formula

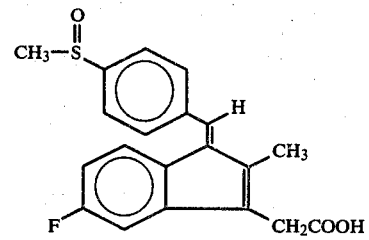

or a therapeutically acceptable salt thereof. The therapeutically acceptable salts are those obtained from appropriate organic or inorganic bases. Preferred salts include these of potassium and the like.

The efficacy of the novel combination in producing antinociceptive properties is particularly seen in acetylcholine bromide abdominal constriction assay of Collier et al [(Brit. J. Pharmacol. Chemotherap. 32, 295–310 (1968)] sometimes referred to as the "mouse writhing test." In the test, mice are dosed with test drug combinations and thereafter injected interperitoneally with acetylcholine bromide and the abdominal constriction responses or block of abdominal constriction responses are observed and compared with control operations.

More specifically, in an operation carried out substantially as described by Collier and co-workers, non-fasted albino mice weighing 18–24 grams were dosed with combinations of one test drug in selected fixed doses together with a second test drug at variable doses for each fixed dose. These were compared with animals dosed with (a) the first test drug at the same doses used in combination but employing saline instead of the second drug, (b) the second test drug at the doses used in combination but employing saline instead of the first drug, and (c) a saline control containing no drug. Each of the drugs, when separately employed, were found to be inactive in the acetylcholine bromide abdominal constriction test at the test dose level.

In carrying out the tests, the test compositions and the control compositions both with and without drugs were administered orally to the test mice. After about 30 minutes the mice were injected intraperitoneally with acetylcholine bromide and the abdominal constriction responses compared (corrected for saline responses as necessary). The results are expressed as percent block.

When the percent block of abdominal constriction observed with the fixed dose was 5 percent or more, the percent block observed with each of the combination dosage levels was corrected with respect to the percent block observed with a fixed dose drug using Abbott's formula for natural mortality.

Likewise, when the response to acetylcholine bromide in the saline control group was 95 percent or less, the response observed with each of the variable dosage levels used in the $ED_{50}$ determination was similarly corrected using Abbott's formula for natural mortality. $ED_{50}$ and 95 percent confidence limits were calculated according to Finney's probit analysis procedure. (Finney, D. J. 1964, Probit Analysis, Second Edition, University Press, Cambridge.) All $ED_{50}$ for a given comparison were calculated using a common slope following a test for parallelism. All paired dose response curves were found to be parallel.

Employing the above-described procedures, potentiation of the analgesic properties of a (Z)-5-fluoro-2- methyl-1-{[4-methylsulfinyl)phenyl]methylene}-1H-indene-3-acetic acid compound (hereinafter sometimes referred to as "sulindac compound") by acetaminophen may be demonstrated. The property is illustrated by employing sulindac (acid form) but is to be understood that it is not limited thereto.

Non-fasted male albino mice weighing 18–24 grams were dosed initially per os (p.o.) with sulindac at various doses and with saline as seen in Tables IA and IB and fifteen minutes later with acetaminophen at 25 mg/kg or at 50 mg/kg. All dose levels of test drug and saline control were given as and are expressed as per os. Twenty mice were employed for each dosage level. As controls, a similar number of mice were dosed with (a) acetaminophen (25 mg/kg) plus saline (5 ml/kg) or acetaminophen (50 mg/kg) plus saline (5 ml/kg) and (b) double dose of saline (5 ml/kg). Sulindac was administered as an aqueous suspension. Acetaminophen was administered as an aqueous suspension.

Thirty minutes after administration of sulindac (and 15 minutes after administration of acetaminophen), the mice were injected intraperitoneally (i.p.) with 5.5 mg/kg of acetylcholine bromide and observed for the presence or absence of the abdominal constriction response. $ED_{50}$ values were determined from the observed values applying where pertinent corrections previously discussed. The results are seen in Tables IA and IB.

(Where "mg/kg" or "ml/kg" is employed, "kg" is in reference to body weight.)

TABLE I-A

Antinociceptive activity of sulindac and acetaminophen in the mouse body constriction assay. Time 30 minutes post sulindac, 15 min. post acetaminophen.

| Treatment | SULINDAC Dose mg/kg po | OBSERVATION No. Responding No. Injected | % Block | Corrected % Block | SULINDAC $ED_{50}$ (95% C.L.***) mg/kg po |
|---|---|---|---|---|---|
| Sulindac plus | 25 | 2/20 | 90 | 88* | |
| Saline 5 ml/kg po | 15 | 6/20 | 70 | 65* | 12.3 (9.4–16.1) |
| | 10 | 11/20 | 45 | 35* | |
| | 7.5 | 13/20 | 35 | 24* | |
| | 5 | 17/20 | 15 | 0* | |
| Sulindac plus | 15 | 1/20 | 95 | 94** | |
| Acetaminophen | 10 | 3/20 | 85 | 81** | 4.6 (3.4–6.3) |
| 25 mg/kg po | 5 | 8/20 | 60 | 50** | |
| | 2.5 | 12/20 | 40 | 25** | |
| | 1.0 | 17/20 | 15 | 0** | |
| Acetaminophen 25 mg/kg po + Saline 5 ml/kg | — | 16/20 | 20 | 6 | |
| Saline 5 ml/kg po + Saline 5 ml/kg po | — | 17/20 | 15 | | |

*% Block in this column corrected for saline response
**% Block in this column corrected for Acetaminophen + saline response
***Confidence Limits

TABLE I-B

Antinociceptive activity of sulindac + acetaminophen in the mouse body constrictive assay. Time 30 minutes post sulindac, 15 min. post acetaminophen.

| Treatment | SULINDAC Dose mg/kg po | OBSERVATION No. Responding No. Injected | % Block | Corrected % Block | SULINDAC $ED_{50}$ (95% C.L.***) mg/kg po |
|---|---|---|---|---|---|
| Sulindac plus | 25 | 4/20 | 80 | 79* | |
| saline 5 ml/kg po | 15 | 8/20 | 60 | 58* | 12.5 (8.8–17.8) |
| | 10 | 12/20 | 40 | 37* | |
| | 5 | 16/20 | 20 | 16* | |
| | 2.5 | 17/20 | 15 | 11* | |
| Sulindac plus | 20 | 0/20 | 100 | 100** | |
| Acetaminophen | 10 | 3/20 | 85 | 79** | |
| 50 mg/kg po | 5 | 6/20 | 70 | 57** | 3.3 (1.9–5.7) |
| | 2.5 | 9/20 | 55 | 36** | |
| | 1.0 | 12/20 | 40 | 14** | |
| Acetaminophen 50 mg/kg po + Saline 5 ml/kg po | — | 14/20 | 30 | 26 | |
| Saline 5 ml/kg po + Saline 5 ml/kg po | — | 19/20 | 5 | — | |

*% Block in this column corrected for saline response
**% Block in this column corrected for Acetaminophen + saline response
***Confidence Limits The foregoing results illustrate the potentiation of the analgesic or antinociceptive properties of a sulindac compound by acetaminophen.

The process of the present invention, namely, a method of producing analgesia, comprises orally administering to subjects, i.e., human and other warm-blooded animals suffering from pain, a sulindac compound and to have an antinociceptive effect. The agents may be administered siluntaneously or sequentially and either agent may be administered first. By the administration of the amounts of the agents as hereinafter set forth, an antinociceptive interaction between the drugs is achieved which is wholly unexpected from the known properties of the components. The active agents may be administered with or without carrier. One method of administration is by use of compositions in unit dosage form which provides a convenient simultaneous administration method.

From the foregoing test results on mice and the known dosage ranges of the components as applied to man when employed alone, it is determined that generally from about 0.1 to 1.7 mg/kg of sulindac compound may be employed together with from about 1.0 to 7.5 mg/kg of acetaminophen; preferably from about 0.17 to 1.5 mg/kg of sulindac compound with from about 1.7 to 7.1 mg/kg of acetaminophen. These amounts when expressed as doses suitable for man are in the range of from about 6 to 100 milligrams of sulindac compound and from about 65 to 450 milligrams of acetaminophen; preferably from about 10 to 90 milligrams of sulindac compound and from about 100 to 425 milligrams of acetaminophen.

The outstanding properties may be effectively utilized by use of the novel pharmaceutical compositions of the present invention. To prepare the pharmaceutical compositions of this invention, a sulindac compound, as primary active agent and acetaminophen as a potentiating agent, are intimately admixed with a pharmaceutically acceptable carrier suitable for oral administration. In preparing the compositions in oral dosage form, any of the urual pharmaceutical media may be employed, including liquid carriers such as water, glycols, oils, alcohols and the like for oral liquid preparations such as suspensions, elixirs and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets represent the most advantageous oral dosage form, these compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier.

Examples of such dosage unit forms are tablets, capsules, pills, powder packets, wafers, teaspoonfuls, tablespoonfuls and the like, and segregated multiples thereof. A dosage unit generally will contain from about 6 to 100 milligrams of a sulindac compound as primary active ingredient together with from about 65 to 450 milligrams of acetaminophen. The preferred dosage unit is from about 10 to 90 milligrams of a sulindac compound together with from about 100 to 425 milligrams of acetaminophen.

The following examples are given to illustrate the novel compositions and are not to be construed as limiting the invention in spirit or in scope.

EXAMPLE I 1000 hard gelatin capsules, each containing 10 milligrams of sulindac as primary active ingredient and 425 milligrams of acetaminophen as potentiating agent are prepared from the following formulation:

|  | Grams |
| --- | --- |
| Sulindac | 10 |
| Acetaminophen | 425 |
| Starch | 250 |
| Lactose | 750 |
| Talc | 250 |
| Calcium stearate | 10 |

A uniform mixture of the ingredients is prepared by blending, and used to fill two-piece hard gelatin capsules. The capsules are suitable to be used for providing satisfactory analgesic effect upon administration to subjects suffering from pain.

EXAMPLE II 1000 compressed tablets, each containing as the primary active ingredient 10 milligrams of sulindac and 425 milligrams of acetaminophen as potentiating agent are prepared from the following formulation:

|  | Grams |
| --- | --- |
| Sulindac | 10 |
| Acetaminophen | 425 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

What is claimed is:

1. A pharmaceutical composition suitable for reducing pain in dosage unit form comprising an effective antinociceptive amount in combination of
(1) as primary agent, from about 6 to 100 milligrams of a compound selected from (a) (Z)-5-fluoro-2-methyl-1-{[4-(methylsulfinyl)-phenyl]-methylene}1H-indene-3-acetic acid having the formula

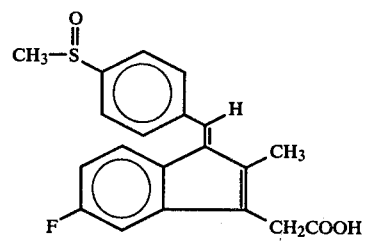

and (b) non-toxic therapeutically acceptable salts thereof, and
(2) as potentiating agent, from about 65 to 450 milligrams of acetaminophen; wherein said primary and said potentiating agents are in admixture with a pharmaceutically acceptable carrier.

2. A composition according to claim 1 in which the primary active agent is (Z)-5-fluoro-2-methyl-1-{[4-(methylsulfinyl)phenyl]methylene}-1H-indene-3-acetic acid.

3. A composition according to claim 1 in which the dosage unit form is a tablet.

4. A composition according to claim 1 in which the dosage unit form is a capsule.

5. A method for producing analgesia which comprises orally administering to a subject suffering from pain
(1) as primary active agent from about 0.1 to 1.7 mg/kg of body weight of a (Z)-5-fluoro-2-methyl-1-{[4-(methylsulfinyl) phenyl]methylene}-1H-indene-3-acetic acid compound, said compound selected from (a) (Z)-5-fluoro-2-methyl-1-{[4-(methylsulfinyl) phenyl]methylene}-1H-indene-3-acetic acid having the formula

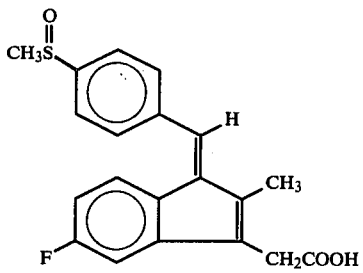

and (b) a non-toxic therapeutically acceptable salt thereof, and (2) as potentiating agent from about 0.1 to 7.5 mg/kg of body weight of acetaminophen.

6. A method according to claim 5 in which the primary active agent is employed in an amount from about 0.17 to 1.5 mg/kg of body weight and acetaminophen is employed in an amount of from 1.7 to 7.1 mg/kg of body weight.

7. A method for producing analgesia which comprises orally administering to a subject suffering from pain
(1) as primary active agent from about 6 to 100 milligrams of a (Z)-5-fluoro-2-methyl-1-{[4-(methyl-sulfinyl)phenyl]methylene}-1H-indene-3-acetic acid compound, said compound selected from (a) (Z)-5-fluoro-2-methyl-1-{[4-(methylsulfinyl)phenyl)]-methylene}-1H-indene-3-acetic acid and (b) the non-toxic therapeutically acceptable salts thereof; and
(2) as potentiating agent from about 65 to 450 milligrams of acetaminophen.

8. A method according to claim 7 wherein the (Z)-5-fluoro-2-methyl-1-{[4-(methylsulfinyl)phenyl]-methylene}-1H-indene-3-acetic acid is administered in an amount in the range of from about 10 to 90 milligrams and acetaminophen in an amount in the range of from 100 to 425 milligrams.

* * * * *